United States Patent [19]

Krüger

[11] 4,113,733
[45] Sep. 12, 1978

[54] PROCESS FOR MAKING 5-AMINO-1,2,3-THIADIAZOLES

[75] Inventor: Hans Krüger, Berlin, Fed. Rep. of Germany

[73] Assignee: Schering AG, Berlin & Bergkamen, Fed. Rep. of Germany

[21] Appl. No.: 823,526

[22] Filed: Aug. 9, 1977

[30] Foreign Application Priority Data

Aug. 13, 1976 [DE] Fed. Rep. of Germany ....... 2636994

[51] Int. Cl.² .......................................... C07D 285/06
[52] U.S. Cl. .............................. 260/306.8 D; 560/159
[58] Field of Search ............................... 260/306.8 D

[56] References Cited

PUBLICATIONS

Huro et al., *J. Am. Chem. Soc.*, 77, 5359–5364 (1955).

*Primary Examiner*—Alton D. Rollins
*Attorney, Agent, or Firm*—Michael J. Striker

[57] ABSTRACT

5-amino-1,2,3-thiadiazoles of the formula

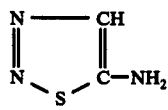

I are made by reacting halogenoacetaldehydes of the formula

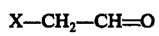

II with hydrazine derivatives of the formula

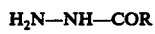

III preferably in an aqueous medium or in a mixture of an aqueous medium with organic solvents so as to form acylhydrazones of the formula

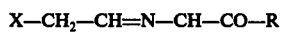

IV whereupon the latter are reacted with thionylchloride of the formula

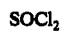

V whereby 5-halogeno-1,2,3-thiadiazoles are formed which are then reacted with ammonia preferably in the presence of a catalyst such as a mineral acid or Lewis acid whereby the desired product is obtained. The products are useful in making plant protection agents and herbicides such as the 1,2,3-thiadiazolyl-urea derivatives.

12 Claims, No Drawings

PROCESS FOR MAKING 5-AMINO-1,2,3-THIADIAZOLES

BACKGROUND OF THE INVENTION

The invention relates to a process for making 5-amino-1,2,3,-thiadiazoles.

Two processes are already known for making these compounds.

One process is based on a reaction of diazomethane with acyl mustard oil (J. Goerdeler and G. Gnad, Ber. 99, 1618, 1966). Considering the explosive nature and toxicity of the diazomethane and the low yield of about 32% this process has not been found useful for industrial production of the 5-amino-1,2,3,-thiadiazoles.

The other process involves a sequence of seven reaction steps wherein the amino group is introduced into the thiadiazole ring through a so-called Gabriel synthesis, that is, in the form of an amino protective group (a phthalimido residue), see D. L. Pain and R. Slack, J. Chem. Soc. 5166–76, 1965. This process likewise is not suited for industrial production since it is rather costly because of the seven reaction steps and also had only a low yield of about 35% and furthermore involves formation of phthalic acid hydrazide for which there is no further use. It also requires large capacity vessels and high amounts of energy.

It is therefore an object of the present invention to provide a process for making 5-amino-1,2,3-thiadiazoles in comparatively few steps and with good yields and thus to provide for an industrially useful method of making these compounds.

SUMMARY OF THE INVENTION

This object is solved by a process wherein
[a] halogenoacetaldehydes of the formula

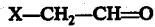
X—CH₂—CH=O            II or acetals thereof are reacted, if desired in the presence of mineral acids with hydrazine derivatives of the formula

H₂N—NH—COR            III preferably in an aqueous medium or in a mixture of an aqueous medium with organic solvents so as to form acylhydrazones of the formula

X—CH₂—CH=N—NH—CO—R    IV

[b] reacting the acylhydrazones with thionylchlorides of the formula

SOCl₂            V so as to form 5-halogeno-1,2,3-thiadiazoles of the formula

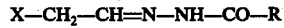

and then
[c] reacting the halogen compounds with ammonia which reaction may take place as a solution in an organic solvent and in the presence of a catalyst, preferably a mineral acid or a Lewis acid, whereby the 5-amino-1,2,3-thiadiazole is formed, X in these reactions being halogen and R being alkoxy, preferably of 1 to 4 carbon atoms, amino or alkylamino, preferably, the alkyl group having 1 to 4 carbon atoms.

The advantages of this process are particularly in the following features:

[1] The reaction of the halogenoacetaldehydes of the formula II with the hydrazine derivative of the formula III can be carried out at temperatures between −20° and +50° C., preferably between 0° and 20° C.;

[2] the reaction of the acylhydrazones of the formula IV with thionylchloride is effected at temperatures between −20° and +100° C. preferably between −5° and 50° C.; and

[3] the reaction between the 5-halogeno-1,2,3-thiadiazoles of the formula IV with ammonia can be effected at temperatures between −70° and +120° C. and at a pressure between 1 and 10 atmospheres, preferably at 1 atmosphere pressure.

The process of the reaction is best illustrated by the following reaction scheme

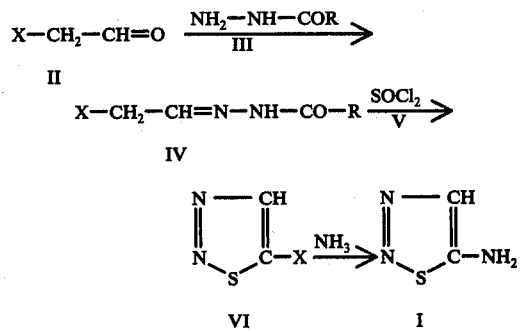

The reaction involves initially production of the 1,2,3-thiadiazole system and then introduction of the amino function by substitution for the halogen atom by means of ammonia.

Necessary are preferably only three stages of synthesis which proceed from inexpensive basic chemicals.

This low number of steps, the use of generally available basic chemicals and the easy course of the synthesis show that the process is a technical breakthrough of a definitely superior nature.

The yields in addition are surprisingly very high since the second stage already ends with a relatively high yield of about 65% or higher and the first and third stage even come out with a quantitative yield so that the total yield throughout the entire reaction is about 50 to 60%.

The synthesis of the acylhydrazones of formula II is effected from halogenoacetaldehydes of formula II by reaction with the hydrazine derivatives of formula III, preferably in an aqueous medium. The halogenoacetaldehydes are preferably used in the form of an aqueous solution. In actual practice of the invention the hydrazine component is added in dilute form in batches or also together with a solvent such as water or an alcohol of 1 to 4 carbon atoms to a solution of the aldehyde which is diluted with water or alcohol. The addition of the reactants can also be effected in reverse order. The reaction takes place at between −20° and 50° C., preferably between 0° C. and 20° C.

DETAILS OF THE INVENTION AND PREFERRED EMBODIMENTS

The solid reaction products upon completion of the reaction of the invention can be obtained by filtration by freeze-drying or by removal of the solvent. They are isolated in the form of colorless crystals. They can easily be recrystallized from organic solvents such as ketones, alcohols, nitriles, esters, ethers and chlorinated hydrocarbons such as acetonitrile, methanol, ethanol, acetic ester or chloroform. They are stable at room temperature. They can, however, also be used for further reactions without recrystallization in dry condition.

The degree of purity of the reaction products can be increased by filtering the dilute commercial halogenoacetaldehyde solution by means of a diatomaceous filter aid such as the commercially avaiable Celites.

The acylhydrazones of the formula IV can also be obtained from the corresponding halogenoacetaldehyde acetals. The acetal for this purpose is used in an aqueous medium and, if desired, in mixture with an organic solvent such as an alcohol or ether, like methanol, ethanol or tetrahydrofuran. To this are added mineral acids, such as sulfuric acid or hydrochloric acid. The splitting off of the acetal occurs quickly at temperatures between 0° and 100°, preferably at the boiling temperature of the solvent. After 15 minutes boiling the reaction mixture is cooled to room temperature and is reacted with the hydrazine component in a diluted or undiluted solvent. The addition of the reactants can be done also in reverse order.

The formed acylhydrazones of the formula IV are then reacted with thionylchloride to form the 5-halogeno-1,2,3-thiadiazoles of formula VI. This reaction is carried out at temperatures between −20° and 100° C., preferably between −5° C. and +50° C. The reaction time will depend on the reaction temperature and may be between 1 and 20 hours.

For the purposes of the synthesis of the 5-halogeno-1,2,3-thiadiazoles the reaction components may be used in about equimolar amounts. Thionylchloride can also be used in a large excess in which case it functions like a solvent.

The acylhydrazones and the thionylchlorides are, however, preferably reacted at a molar ratio of 1:3.

The reaction can also be carried out in the presence of solvents which are inert towards the reaction components. Such are, for instance, halogenated hydrocarbons like methylene chloride, chloroform and carbon tetrachloride, aliphatic and aromatic hydrocarbons, such as petroleum ether, pentane, cyclohexane, benzene, toluene and xylene, and ethers like diethylether, tetrahydrofuran, dioxane, ethyleneglycoldiethylether and diethyleneglycoldiethylether, and ester, such as acetic acid ester.

The acylhydrazones are usually added in batches to the thionylchloride. The acylhydrazones may be dissolved or suspended in a suitable solvent and the thionylchloride may also be diluted with an organic solvent. These reactants can also be brought together in reverse order.

The hydrogen chloride which forms during the reaction can continuously be removed by means of a stream of inert gas from the reaction vessel.

The further processing of the reaction mixture after completing the reaction is effected in conventional form.

After distilling off the solvent and the excess thionylchloride the residue can be subjected to fractional distillation. The excess thionylchloride can also be destroyed with a saturated sodium carbonate solution, sodium or potassium bicarbonate solution, sodium acetate solution or with sodium or potassium hydroxide or directly with water. The reaction solution is then subjected to a steam distillation.

Because of their high density the 5-halogeno-1,2,3-thiadiazoles can easily be removed from the steam condensates. The aqueous phase can further be extracted with pentane, ether or methylene chloride.

The reaction products are obtained from the steam distillation as slightly yellow, highly volatile liquids which have the tendency to solidify to crystals in the condenser. In case of the fractional distillation they are obtained as colorless liquids.

The reaction products are highly soluble in organic solvents such as hydrocarbons, halogenated hydrocarbons, ethers, ketones, alcohols, esters, carboxylic acid amides and carboxylic acid nitriles. Their solubility in water is low.

For further reaction another purification is not necessary even with the crude products obtained by steam distillation. The thus-obtained reaction products depending on their degree of purity have a tendency to darken, particularly when exposed to light, but even after extended periods exhibit hardly any loss of substance.

The 5-halogeno-1,2,3-thiadiazoles are then finally reacted with ammonia to form the 5-amino-1,2,3-thiadiazoles of formula I. Ammonia can be employed in the form of ammoniacal organic solvents, such as in methanol, ethanol, benzene, toluene, xylene, tetrahydrofuran or dioxane or preferably, ammonia is used in liquified condition. The reaction takes place at temperatures between −70° and 120° C., preferably at the reflux temperature of the specific reaction mixture. The pressure may be between 1 and 10 atmospheres, but preferably is 1 atmosphere. The reaction components can be used in molar amounts. However, the ammonia is preferably used in excess and most preferably in an excess of 1 to 20 equivalents.

The reaction can be carried out also with acid or Lewis acid catalysts in the form of an addition-elimination reaction. As Lewis acids the following may be mentioned: $HgCl_2$, $(NH_4)_2SO_4$, $NH_4Cl$, $NH_4Br$, $HgBr_2$, $(CH_3)_3SiOSO_2$, $CF_3$, $SnCl_4$, $BF_3$ and p-toluenesulfonic acid hydrate.

Preferably, one proceeds by adding the halogen components at a temperature between −60° and −35° and atmospheric pressure dropwise to liquid ammonia, and permits the reaction to take place in a period between 1 and 8 hours at reflux temperature.

The various ammonium salts which are formed during the reaction normally catalyze the chlorine exchange. After completion of the reaction the excess ammonia is removed by evaporation and the formed 5-amino-1,2,3-thiadiazole is separated from the ammonium salt by complete extraction with a suitable organic solvent such as acetic acid ester, methylene chloride, acetone, methanol or ethanol or is recrystallized directly from water.

The 5-amino-1,2,3-thiadiazoles are thus obtained in highly pure form and in almost quantitative yields. For further reactions no subsequent purification steps are necessary.

The following examples will further illustrate the process of the invention.

EXAMPLE 1a

Making of 2-chloroethylideneaminocarbamic acid ethylester 550 g (3.5 mol) of a 50% aqueous solution of chloroacetaldehyde were diluted with 3000 ml water and were reacted with 10 g Celite 545 in order to react with the precipitating resin. For this purpose the solution was passed through a fluted filter into a three times tubulated round bottom flask of 6 l contents which was provided with a stirrer and thermometer. While cooling with ice a solution of 364 g (3.5 mol) of hydrazinoformicacid ethylester in 360 ml water was added during a period of 15 min. The temperature within the reaction vessel was maintained at between 0° and 5° C. There formed immediately a thick white crystal slurry. Stirring was continued at room temperature for 30 minutes. The crystals were then removed by suction, were washed neutral with about 6 liters water and were dried in a vacuum at 30° C. until the weight remained constant.

The yield was 525.98 g = 91.3% of the theoretical value. M.p. 120°–121° C.

The compound could also be recrystallized from alcohol.

Analysis: Calculated: C, 36.48%; H, 5.51%; Cl, 21.54%; N, 17.02%. Obtained: C, 36.91%; H, 5.46%; Cl, 21.37%; N, 16.93%.

EXAMPLE 1b

Making of 2-chloroethylideneaminocarbamic acid ethylester 60 ml water and 0.8 ml of concentrated hydrochloric acid were heated to 90° C. in a three times tubulated round bottom flask of 250 ml contents equipped with a stirrer, thermometer and reflux condenser. The reaction mass was then reacted with 15.2 g of chloroacetaldehydediethylacetal and was subjected to stirring for 15 minutes at 90° to 100° C. The mass was then cooled to 30° C. and a solution of 12.5 g of hydrazinoformic acid ethylester in 40 ml water was added within a period of 10 minutes. There formed a white crystal slurry. After further stirring for 15 minutes the mass was subjected to suction. The separated crystals were washed with 30 ml icewater and were dried in vacuum at room tempeture until the weight remained constant. There were obtained white crystals.

Yield: 14.4 g = 87.5% of the theoretical value.
M.p.: 120°–121° C.

In an analogous manner the following compounds were made:

| Compound | Physical Constants |
|---|---|
| 2-bromoethylideneaminocarbamic acid ethylester | m.p. : 126–127° C |
| 2-chloroethylideneaminocarbamic acid methylester | m.p. : 129–130° C |
| chloroacetaldehydesemicarbazone | m.p. : 132–133° C |

EXAMPLE II

Making of 5-chloro-1,2,3-thiadiazole 110 ml of thionylchloride (1.5 mol) were cooled to 5° C. in a three times tubulated round bottom flask of 2 liter contents equipped with a stirrer, thermometer, reflux condenser and gas discharge duct. The thionylchloride was then reacted within 5 minutes with 82.3 g of 2-chloroethylideneaminocarbamic acid ethylester. The temperature within the reaction vessel rose to 20° C. The mass was then stirred for 15 minutes on ice whereupon stirring was continued for 2 hours at room temperature. A dark green reaction solution formed upon evolution of gas.

After standing for 15 hours at room temperature the reaction solution which now had a brown color was slowly reacted with 600 ml of a saturated sodium bicarbonate solution at a temperature within the vessel between 5° and 20° C. The mass was then subjected to steam distillation. One liter of distillate was collected. The chlorothiadiazole precipitated as a yellow liquid. It was then separated and the distillate was extracted twice with 200 ml pentane each. The cooled product was dried together with the pentane extracts over $MgSO_4$ and was subjected to concentration in a vacuum at 40° C. and 200 mm pressure.

Yield: 46.0 g in the form of the crude product which can be used for the next reaction step without further distillation.

However, if distillation was effected the yield was 39.1 g = 65.1% of the theoretical value of 5-chloro-1,2,3-thiadiazole; $bp_{30}$: 58°–62° C.; m.p.: about 20° C.

Analysis: Calculated: C, 19.92%; H, 0.84%; Cl, 29.41%; N, 23.24%. Found: C, 20.14%; H, 1.01%; Cl, 31.00%; N, 23.22%.

In an analogous manner there was formed 5-bromo-1,2,3-thiadiazole; $bp_{30}$: 61°–64° C.

EXAMPLE III 5-amino-1,2,3-thiadiazole 200 ml of condensed ammonia were placed in a three times tubulated round bottom flask of 1 liter contents which was provided with a dry ice condenser and a magnet stirrer. A dry ice/methanol bath was provided to obtain a temperature of −75° C. Within a period of 5 minutes there were then added 50 g (0.415 mol) of 5-chloro-1,2,3-thiadiazole. Yellow crystals immediately separated out. Without the cold temperature bath stirring was continued under reflux. After about 1 hour an almost clear yellow solution had formed. The ammonia was evaporated at room temperature within 2½ hours.

Subsequently, the mass was subjected for half an hour with a water jet pump to a vacuum to completely remove the ammonia. The remaining residue in the flask was digested several times with altogether 900 ml acetic acid ester under stirring and boiling. The acetic acid solutions were then concentrated by evaporation in a vacuum at 40° C. up to dryness.

Yield: 36.1 g = 85.9% of the theoretical value. m.p.: 137°–138° C.

The obtained compound formed a clear solution in acetone.

The product of these reactions is valuable for making protective plant agents and herbicides, for instance herbicidally active 1,2,3-thiadiazolyl-urea derivatives.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A process for making 5-amino-1,2,3-thiadiazoles of the formula

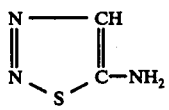

the said process comprising

[a] halogenoacetaldehydes of the formula

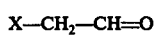    II or acetals thereof are reacted with hydrazine derivatives of the formula

    III so as to form acylhydrazones of the formula

    IV

[b] reacting the acylhydrazones with thionylchlorides of the formula

    V so as to form 5-halogeno-1,2,3-thiadiazoles of the formula

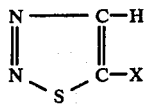    VI and then

[c] reacting the halogen compounds with ammonia whereby the 5-amino-1,2,3-thiadiazole is formed,
X in these reactions being halogen and R being alkoxy, amino or alkylamino.

2. The process of claim 1 wherein the reaction at [a] is carried out in the presence of a mineral acid.

3. The process of claim 1 wherein the reaction at [a] is carried out in an aqueous medium or in a mixture of an aqueous medium with an organic solvent.

4. The process of claim 1 wherein the reaction at [c] is carried out with an ammonia dissolved in an organic solvent.

5. The process of claim 1 wherein the reaction at [c] is carried out in the presence of a mineral acid or a Lewis acid as catalyst.

6. The process of claim 1 wherein if R is alkoxy or alkylamino the alkyl group has 1 to 4 carbon atoms.

7. The process of claim 1 wherein the reaction at [a] is carried out at a temperature between $-20°$ and $50°$ C.

8. The process of claim 7 wherein the temperature is between about $0°$ and $20°$ C.

9. The process of claim 1 wherein the reaction at [b] is carried out at a temperature between $-20°$ and $100°$ C.

10. The process of claim 9 wherein the temperature is between $-5°$ and $50°$ C.

11. The process of claim 1 wherein the reaction with ammonia at [c] is carried out at a temperature between $-70°$ and $120°$ C. and at a pressure between 1 and 10 atmospheres.

12. The process of claim 11 wherein the pressure is about 1 atmosphere.

* * * * *